(12) United States Patent
Machiraju

(10) Patent No.: US 7,727,276 B2
(45) Date of Patent: Jun. 1, 2010

(54) SYSTEM AND METHOD FOR HEART VALVE REPLACEMENT

(76) Inventor: Venkat R. Machiraju, 534, Squaw Run Rd. East, Pittsburgh, PA (US) 15238

( * ) Notice: Subject to any disclaimer, the term of this patent is extended or adjusted under 35 U.S.C. 154(b) by 585 days.

(21) Appl. No.: 11/732,593

(22) Filed: Apr. 4, 2007

(65) Prior Publication Data
US 2007/0244558 A1 Oct. 18, 2007

Related U.S. Application Data

(60) Provisional application No. 60/792,260, filed on Apr. 14, 2006.

(51) Int. Cl.
A61F 2/24 (2006.01)
(52) U.S. Cl. .................................. 623/2.11
(58) Field of Classification Search ............. 623/2.11, 623/2.17–2.18, 2.38–2.39, 2.4–2.41
See application file for complete search history.

(56) References Cited

U.S. PATENT DOCUMENTS

| | | | | |
|---|---|---|---|---|
| 3,491,376 A | * | 1/1970 | Shiley | 623/2.34 |
| 3,839,741 A | * | 10/1974 | Haller | 623/2.34 |
| 4,035,849 A | * | 7/1977 | Angell et al. | 623/2.15 |
| 4,416,029 A | | 11/1983 | Kaster | |
| 4,535,483 A | * | 8/1985 | Klawitter et al. | 623/2.4 |
| 4,705,516 A | * | 11/1987 | Barone et al. | 623/2.39 |
| 4,725,274 A | * | 2/1988 | Lane et al. | 623/2.18 |
| 5,332,402 A | * | 7/1994 | Teitelbaum | 623/2.42 |
| 5,370,685 A | | 12/1994 | Stevens | |
| 5,545,214 A | | 8/1996 | Stevens | |
| 5,549,665 A | * | 8/1996 | Vesely et al. | 623/2.14 |
| 5,571,175 A | * | 11/1996 | Vanney et al. | 623/2.41 |
| 5,584,879 A | * | 12/1996 | Reimold et al. | 623/2.36 |
| 5,716,370 A | * | 2/1998 | Williamson et al. | 606/153 |
| 5,776,188 A | * | 7/1998 | Shepherd et al. | 623/2.38 |
| 5,908,428 A | | 6/1999 | Scirica et al. | |
| 5,928,281 A | * | 7/1999 | Huynh et al. | 623/2.14 |
| 5,980,569 A | | 11/1999 | Scirica | |
| 5,984,959 A | | 11/1999 | Robertson et al. | |
| 6,042,607 A | * | 3/2000 | Williamson et al. | 623/2.11 |
| 6,096,074 A | | 8/2000 | Pedros | |
| 6,176,877 B1 | * | 1/2001 | Buchanan et al. | 623/2.39 |
| 6,203,553 B1 | | 3/2001 | Robertson et al. | |
| 6,217,546 B1 | | 4/2001 | Hinchliffe et al. | |
| 6,217,611 B1 | * | 4/2001 | Klostermeyer | 623/2.38 |

(Continued)

*Primary Examiner*—(Jackie) Tan-Uyen T Ho
*Assistant Examiner*—Son Dang
(74) *Attorney, Agent, or Firm*—Rama Nath

(57) ABSTRACT

A prosthetic heart valve replacement system and method aim to reduce the time duration of the patient on the heart-lung machine during surgery. In one embodiment, the invention uses a two rings (e.g., of Titanium) comprising a first outer anchoring ring installed in a first step in the patient annulus, e.g., by stapling (e.g., using Nitinol® staples), and a second inner valve ring which has apertures and to which the sewing cuff of prosthetic heart valve (e.g., of Dacron) is sutured around the sewing cuff. The suturing is expediently completed outside of the patient's body, parallel with the stapling of the anchoring ring in the patient annulus. The inner valve ring may have circumferential resiliency. The inner valve ring along with the fastened/sutured prosthetic valve is installed snugly (in a second step) to be captively retained concentrically within the already installed outer anchoring ring, to complete the heart valve replacement.

16 Claims, 5 Drawing Sheets

U.S. PATENT DOCUMENTS

| | | | |
|---|---|---|---|
| 6,241,765 B1 * | 6/2001 | Griffin et al. | 623/2.38 |
| 6,338,735 B1 | 1/2002 | Stevens | |
| 6,350,282 B1 * | 2/2002 | Eberhardt | 623/2.13 |
| 6,402,780 B2 * | 6/2002 | Williamson et al. | 623/2.11 |
| 6,413,274 B1 * | 7/2002 | Pedros | 623/2.11 |
| 6,569,196 B1 * | 5/2003 | Vesely | 623/2.14 |
| 6,676,671 B2 * | 1/2004 | Robertson et al. | 606/139 |
| 6,716,243 B1 * | 4/2004 | Colvin et al. | 623/2.4 |
| 6,767,362 B2 * | 7/2004 | Schreck | 623/2.11 |
| 6,945,997 B2 * | 9/2005 | Huynh et al. | 623/2.17 |
| RE40,377 E * | 6/2008 | Williamson et al. | 623/2.11 |
| 7,585,321 B2 * | 9/2009 | Cribier | 623/2.14 |
| 2001/0047207 A1 * | 11/2001 | Michelson | 623/17.11 |
| 2004/0266031 A1 * | 12/2004 | Inomata | 438/3 |
| 2005/0182482 A1 * | 8/2005 | Wang et al. | 623/1.15 |
| 2005/0246020 A1 * | 11/2005 | Southworth | 623/16.11 |
| 2007/0129795 A1 * | 6/2007 | Hill et al. | 623/2.11 |

\* cited by examiner

ANCHORING RING

TOP

SIDE

Aortic anchoring ring

Mitral anchoring ring

VALVE RING

TOP

SIDE

ANCHORING RING

SYSTEM AND METHOD FOR HEART VALVE REPLACEMENT

RELATED APPLICATIONS

Benefit is claimed under 35 U.S.C. 119(e) to U.S. Provisional Application Ser. No. 60/792,260, entitled "System and a Method for Heart Valve Replacement" by Venkat R Machiraju, filed on Apr. 14, 2006, which is herein incorporated in its entirety by reference for all purposes.

FIELD OF THE INVENTION

This invention relates generally to heart valve replacements, and more particularly to a system and method for surgical heart valve replacement performed with due consideration to the time during which a patient needs to be kept on the heart-lung machine during the valve replacement.

BACKGROUND OF THE INVENTION

Heart valve replacement surgeries are very commonly performed all over the world, and presently, at least 90,000 heart valve replacements are performed each year in the United States alone, and more than 500,000 are performed all across the globe. Current surgical heart valve implantation is a highly skilled surgical procedure and invariably takes prolonged time duration. During this procedure the patient is on cardiopulmonary bypass and is subjected to the adverse effects of such prolonged bypass time.

Presently, during heart valve replacements, trauma to blood on the heart lung machine is known to lead to various bleeding complications and also end organ failure. Minimizing the cardio pulmonary bypass time is the main objective of seeking new advances in heart valve implantation procedures. The minimized bypass time should improve clinical outcomes greatly and decrease overall patient mortality.

Ever since the heart lung machine was invented in 1953, various cardiac surgical procedures have been performed, and Hufnagal implanted the first mechanical prosthesis in a descending thoracic aorta to inaugurate the concept of prosthetic valve implantation. The prior art technique of implanting a prosthetic valve (having a Dacron® sewing ring) on the valve annulus basically involved applying a multiplicity of Teflon-pledgeted sutures sequentially around the aortic (or mitral) annulus and passing a plurality of needles (two for each suture) through the Dacron® sewing ring of the prosthetic valve and tying the knots in place to secure the prosthetic valve to the patient's annulus for implantation.

Implantation of sutureless valves using staples only, has been attempted in the past, and, Magovern-Cromie sutureless valves were implanted in 1963. Both Mitral and Aortic prosthetic sutureless valves were clinically implanted with varying results and success. In such installations however, perivalvular leaks were reportedly a problem along with heart blocks.

There are examples of heart valve replacement tools and procedures with differing results and practical limitations. U.S. Pat. No. 5,984,959 to Robertson et al teaches an expandable heart valve installation assembly and an expandable ring installation assembly. U.S. Pat. No. 6,096,074 to Pedros teaches a stapling apparatus and method for heart valve replacement wherein a plurality of staples having sutures attached thereto, are discharged from a surgical stapler into the heart. U.S. Pat. No. 6,203,553 B1 to Robertson et al teaches a stapling apparatus having a first cylindrical portion, and a second concentric cylindrical portion with a camming arm configured to cam a staple assembly outwards in a radial direction. U.S. Pat. No. 6,676,671 B2 to Robertson et al teaches a stapling apparatus with a first cylindrical portion having a cam, a concentric second cylindrical portion and a third cylindrical portion concentric about the second cylindrical portion and having an anvil flange. The heart valve stapling arrangements known hitherto have disadvantages in terms of exposing the patient to prolonged durations on the heart-lung machine during the valve replacement.

There is therefore a need for a system and method for heart valve replacement obviating the disadvantages of prior art and reducing the cardio pulmonary bypass time for the patient.

SUMMARY OF THE INVENTION

The present invention provides a heart valve replacement system and method enabling a reduction of the time duration (—patient machine time—) that the patient is subjected to the heart-lung machine during the prosthetic heart valve implantation. Without the invention, the patient machine time could be in excess of an hour, whereas, with the system and method taught herein, the patient machine time could be of the order of 10 minutes, which is a considerable reduction. One embodiment of the replacement heart valve system resides in a two ring assembly comprising a first outer anchoring ring which is stapled to the heart valve annulus, and a second inner valve ring to which the prosthetic valve is sutured outside of the patient, the second inner valve ring being captively and snugly held in assembly concentrically inside the first outer anchoring ring. A two ring assembly of the right size is chosen for each patient in question, to obtain the best possible results. For selecting the appropriate size of the two ring assembly, the patient's annulus is sized using appropriate known tools. Expediently, the suturing of the prosthetic valve to the inner valve ring is completed (outside of the patient) parallely with the stapling process of the first outer ring to the patient's annulus, to conserve time.

The invention in a broad form includes a prosthetic heart valve replacement system for valve replacement in a patient's heart valve annulus during surgery, enabling a reduction of time duration that the patient is subjected to a heart-lung machine during the prosthetic heart valve replacement, comprising: a first outer anchoring ring which is separately fastened to the patient's heart valve annulus during surgery, and a second inner valve ring to which the prosthetic heart valve is attached outside of the patient, such as by suturing; the second inner valve ring being configured to be captively and snugly held concentrically inside of the first outer anchoring ring upon assembly. The prosthetic heart valve, as known, is a three leaflet valve for both aortic and mitral replacement, or, may be mono or bicuspid if a mechanical type. Any other type of heart valve is also within the ambit of the present invention. The first outer anchoring ring and the second inner valve ring are made of nonmagnetic material.

In another form the invention resides in a two-ring prosthetic heart valve replacement system for valve replacement in a patient's heart valve annulus during surgery, enabling a reduction of time duration that the patient is subjected to a heart-lung machine during the prosthetic heart valve replacement, comprising: a first outer anchoring ring with a tubular configuration with a shelf at one end and a radially inwardly projecting flange integrally formed at the other end of the tubular configuration, the first outer ring being separately stapled, fastened and installed in the patient's heart valve annulus during surgery; and, a second inner valve ring which is also provided with an open tubular configuration at a first end and an integrally formed radially inwardly extending apertured flange at a second end and configured for permanent attachment to the prosthetic heart valve such as by suturing which is done outside of the patient; the second inner valve ring tubular configuration being configured at its first end to be resilient radially inwards to facilitate assembly thereof concentrically inside of the first outer anchoring ring for being captively and snugly held therein.

The invention also resides in a method of implanting a prosthetic heart valve in a patient, comprising the steps of: excising a defective natural heart valve from an annulus area of the patient and sizing the patient's annulus; in a first step, installing and fastening a first anchoring ring of a suitable size in the patient's annulus, and selecting a suitable sized second valve ring which is configured to be assembled concentrically inside of the first anchoring ring in a captive manner to be snugly held and retained therein; preparing a chosen prosthetic valve by suturing the prosthetic valve outside of the patient's body to said selected suitably sized second valve ring by using a desired number of threads of suturing material; and, in a second step, installing the second valve ring along with the sutured prosthetic valve concentrically inside of the first anchoring ring.

In one embodiment, the first outer anchoring ring is fastened to the patient annulus by staples, and has a generally L shaped cross section with a plurality of perforations along the ring periphery to receive a plurality of staples which might have memory. The staples are dispensed into the perforations of the anchoring ring, being directed radially outwards from the inside of the anchoring ring, and upon installation will pierce the patient's annulus tissue and stay in place, thus fastening and retaining the first outer anchoring ring securely on the patient's annulus. The inner valve ring is provided with a plurality of peripheral apertures, and permanently holds the prosthetic valve with the help of a plurality of sutures which are threaded through the apertures to fasten the periphery of the prosthetic valve in the opening of the inner valve ring. The state of the art prosthetic valves generally have a ring-like periphery known as the "sewing cuff". In the present design and arrangement, sutures bind and fasten the sewing cuff of the prosthetic valve to the inner valve ring in a suturing process which is performed outside of the patient's body during surgery.

The method of implanting the prosthetic valve in one embodiment, resides in sizing the patient's annulus (based on the size of the defective valve to be excised from the patient) for selecting a suitable size of the anchoring ring for installation. A valve ring which is compatible in size with the selected size of the anchoring ring is prepared by attaching a chosen prosthetic valve to the opening of the selected valve ring outside of the patient's body by using the desired number threads of suturing material. The suitable size of anchoring ring is prepared with the desired number of staples assembled into position. In an exemplary method, in a first step, the anchoring ring with the staples in position is installed in the patient's annulus by using a single stroke of a stapling tool that is designed to advance the staples for penetration into the tissue at the site of the patient's annulus. In a second step, the valve ring which is prepared with the prosthetic valve outside of the patient's body, is positioned and pushed into the anchoring ring using another tool for completing a snug captive assembly of the valve ring (with the prosthetic valve) concentrically inside of the already installed anchoring ring. The foregoing two step operation completes the heart valve replacement, following which the patient may be closed up, using the remaining known procedural sequence.

In a preferred embodiment, in order to facilitate the inner valve ring being captively held concentrically inside the anchoring ring in assembly, the vertical portion of the L shaped cross section of the anchoring ring is provided with a step which is so dimensioned as to prevent the assembled inner valve ring from getting easily dislodged. Also, suitable 'v' shaped grooves or other slits are provided in the body of the inner valve ring to impart sufficient circumferential resiliency in a radially inward direction to the inner valve ring to facilitate assembly. Expediently, the inner valve ring may be somewhat tapered to narrow down in the direction of its assembly into the first anchoring ring. Other alternative structural provisions and modifications in the two rings and especially in the anchoring to enable the valve ring to be held snugly in a captive manner after assembly are also acceptable and are within the ambit of the invention. It is important to note that the method and system taught herein are designed to satisfy the requirements of an acceptable heart valve prosthetic replacement, with drastically reduced duration of exposure of the patient to the heart-lung machine during the valve replacement.

BRIEF DESCRIPTION OF THE DRAWING

A more detailed understanding of the invention may be had from the following description of certain exemplary embodiments, to be understood in conjunction with the accompanying drawings, wherein.

DETAILED DESCRIPTION

A detailed description of one or more embodiments of the invention is provided below using the accompanying figures that illustrate by way of example the principles of the invention. While the invention is described in connection with such embodiments, it should be understood that the invention is not limited to any particular embodiment. On the contrary, the scope of the invention is limited only by the claims and the claim-equivalents, noting that the invention encompasses numerous alternatives, modifications and equivalents. For the purpose of example, numerous specific details are set forth in the following description in order to provide a thorough understanding of the present invention.

The present invention may be practiced using the principles of the invention, without some or all of these specific details. For the purpose of clarity, technical material and information that is known in the technical fields related to the invention have not been described in detail so that the present invention is not unnecessarily obscured. It is noted that in accordance with accepted medical practice, the replacement valve in the present procedure comprises a prosthetic valve which includes a Dacron ring that is sutured for installation, using several non absorbable sutures. It is noted that other types and materials for the replacement valve, the anchoring ring and the valve ring are acceptable and are within the purview of this invention.

Figure 4:
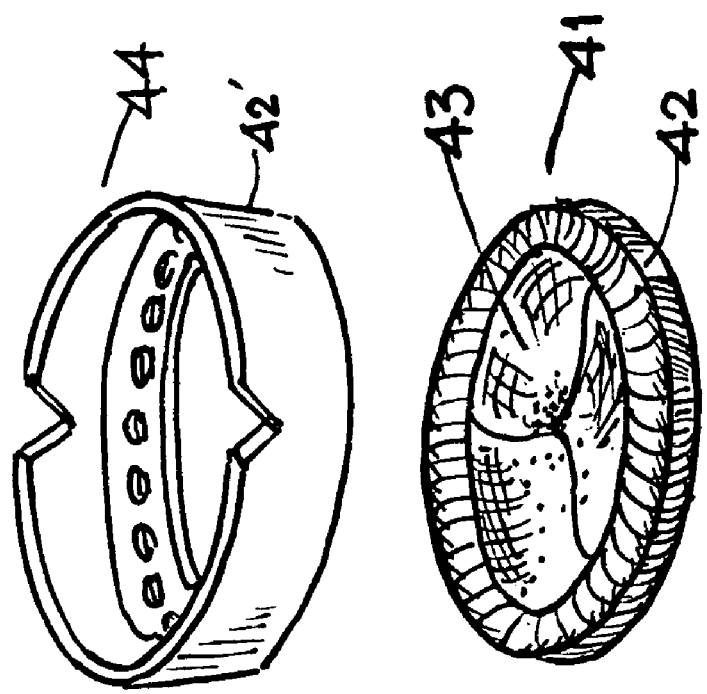
FIG. 4 illustrates an exemplary prosthetic replacement valve made of Dacron® which includes a sewing cuff, which is initially positioned for Mitral replacement outside of the patient for being sutured to the valve ring.

Typically, prosthetic heart valves comprise a Dacron based construction including a ring-like sewing cuff similar to the annular sewing cuff 44 illustrated in FIG. 4. A brief review of the set-backs in the prior art method or process of installing a prosthetic valve in a patient would assist in enabling an appreciation of the features and advantages of the present invention. It is noted that the patient is on the heart-lung machine during the valve replacement surgery. However, after the patient's Aortic or Mitral annulus is prepared for receiving the prosthetic valve, one prior art method resorts to suturing the sewing cuff 44 to the patient's prepared annulus using a multiplicity of suturing threads, each suturing thread being attached to one or two needles as preferred. The sutures are deployed with the patient open on the operating table and on the heart lung machine. The free ends of the sutures are individually threaded through the tissue of the patient's annulus, and finally, all the sutures are pulled up taut and tied, so that the prosthetic valve is installed in place. However, in the prior art process, there are two drawbacks:

1. Considering the limited access to the patient's annulus for suturing the sewing cuff in place, the surgeon painstakingly completes the sutures one by one meticulously around the periphery of the sewing cuff. This prior art process could take in excess of an hour, depending on how good an access the surgeon can have and how many sutures the surgeon prefers to use for circumferential fastening of the sewing cuff in place on the patient's annulus. Needless to say, the patient is exposed to the heart lung machine for a prolonged time period in prior art methods and systems, with possible adverse consequences which are known to those well versed in the field. If on the other hand, the sewing cuff of the prosthetic valve is directly stapled to the patient annulus, there may be blood leaks and consequent problems.

2. There is always a potential that when the sutures between the prosthetic valve and the patient annulus (in the prior art method) are pulled taut and tied, the sutures which are tied might start cutting through the patient annulus tissue with undesirable consequences. Also, in the prior art methods, the extent of the damage caused by the sutures starting to cut through the patient's annulus tissue might not be easily detected or measurable.

The present valve replacement process aims to obviate the disadvantages of prior art approaches and achieves a drastic reduction in the time duration for which the patient is exposed to the heart lung machine, and the time-reduction is highly desirable and sought after by those in the medical profession.

An exemplary Aortic valve Replacement Procedure using the present invention and an ASD (Automatic Stapling Device) is as follows: The standard cardiopulmonary bypass for the patient is initiated. The aorta is cross-clamped and the aorta is opened. The aortic valve is completely excised using the necessary judgment. In this process of removing the patient's aortic valve, any and all of the calcium in the aortic wall is also removed to facilitate subsequent negotiation of the powered tool with the anchoring plate as will be explained later. At this juncture, a standard valve sizer (of any suitable manufacturer) is taken by the surgeon and passed snugly through the valve annulus to ascertain the replacement valve size.

Based on the ascertained replacement valve size, a suitable size for the anchoring ring/valve ring combination is selected. Alternatively, the surgeon can determine the required anchoring ring/valve ring combination size by imaging methods or other techniques known to those skilled in the art. The anchoring ring is stapled to the patient's valve annulus.

Exemplary configuration and structural features of the anchoring ring and the valve ring:

The anchoring ring is referred to herein as the first outer anchoring ring or the anchoring ring and is preferably made of Titanium. In one embodiment, the anchoring ring has a tubular configuration and a wall with a vertical shelf 12 formed within the anchoring ring. The anchoring ring also includes an integral circumferential (horizontal) flange 14 which extends radially inwards from the wall, at one end of the vertical shelf. The vertical shelf (which may have a height of 4 to 5 mm,) is expediently provided with a shelf groove 15 on the inner surface into which the second ring or the valve ring gets clipped in captively. The horizontal flange part of the anchoring ring may have a radial width of 2 to 3 mm, (and preferably no more than 4-5 mm in radial width) and may be 1.5 to 2 mm in thickness. Any other suitable thickness for sufficient mechanical strength is acceptable. The dimensions indicated are only by way of example and not a limitation. The undersurface of the anchoring ring i.e., the undersurface of the horizontal flange part 14 is preferably slightly uneven to be conducive to hug the tissue of the patient's valve annulus tightly. The top surface of the ring may be relatively smooth. After installation, the anchoring ring with its circumferential flange 14 tightly and permanently rests in the patient's annulus.

There are multiple holes/apertures provided along the radial outer edge of the horizontal flange 14 of the anchoring ring, the holes extending through the thickness of the vertical shelf. In one embodiment, Nitinol staples which have memory, and are installed to go through the holes of the anchoring ring for anchoring the anchoring ring to the patient's valve annulus. The outer surface of the anchoring ring all around preferably has a trabeculated Tantalum metal coating. At the top edge of the vertical shelf of the anchoring ring there are optional holes provided all around for any additional sutures if necessary, as will be described hereinafter.

The second ring of the prosthetic device is referred to herein as the second inner valve ring or valve ring or the second ring, which is also a circular short ring preferably made of Titanium, with a tubular configuration and dimensioned to be snugly assembled inside of the anchoring ring to be captively held therein, as will be described in greater detail hereinafter. The tubular configuration of the valve ring has a vertical shelf 22 that has circumferential resilience and an integral horizontal circular flange plate projection radially inwards and with a radial width of 3.5-4.5 mm. The horizontal circular flange plate has a plurality of holes all around the circle into which the sewing cuff of the Dacron prosthetic valve is sutured, as will be described in greater detail hereinafter. The valve ring is so configured that in assembly it gets captively held and retained concentrically inside of the inner shelf edge 15 of the vertical part of the anchoring ring.

The valve ring has preferably 3 or 4 small v shaped cuts on the vertical shelf to provide circumferential resiliency to the vertical shelf thereof to enable the valve ring to be captively held and retained concentrically inside of the anchoring ring. Other alternative structural features to impart circumferential resiliency to the vertical shelf of the valve ring are envisaged and are within the ambit of the invention. For example, the vertical shelf of the valve ring may be provided with one or two slits extending a short length axially from the top end of the vertical shelf.

Figure 1:
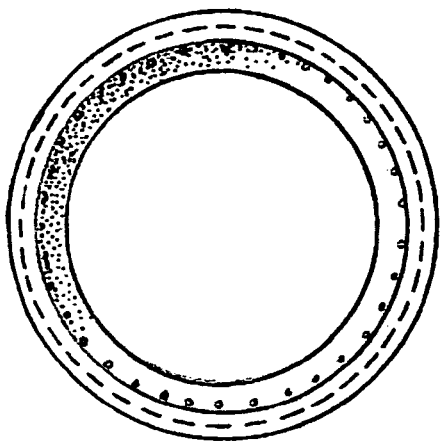
FIG. 1 illustrates an anchoring ring (—which in use is concentrically outer—) as used in the described system and method, differently for Aortic and Mitral implementation.
Figure 1:
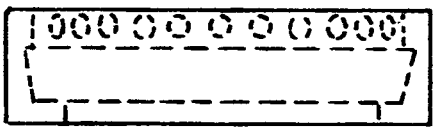
Figure 1:
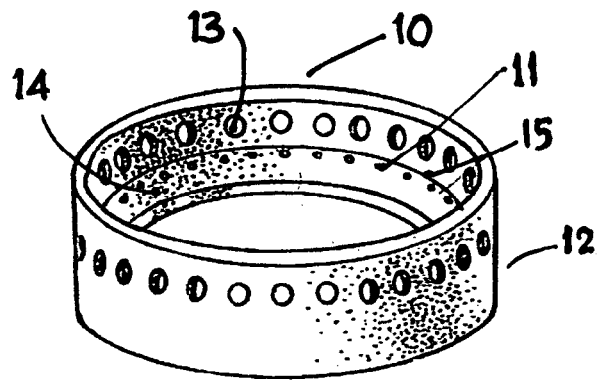
Figure 1:
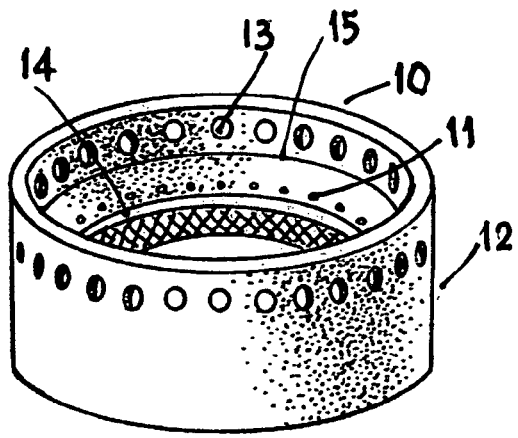

Structurally, the anchoring ring 10 as illustrated in FIG. 1 and described herein, has a well-shaped configuration (vertical shelf) and a generally L shaped cross section having a shelf portion 12, and a plurality of circumferentially placed apertures 11 located expediently close to the meeting edge of the two sides of the L shaped cross section.

Figure 2:
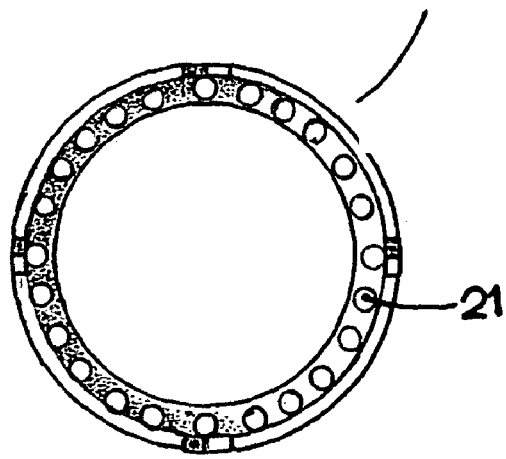
FIG. 2 illustrates a valve ring (—which is installed concentrically inner—) as used in the described system and method.
Figure 2:
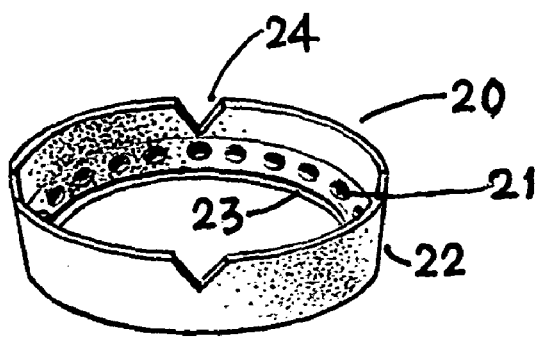
Figure 2:
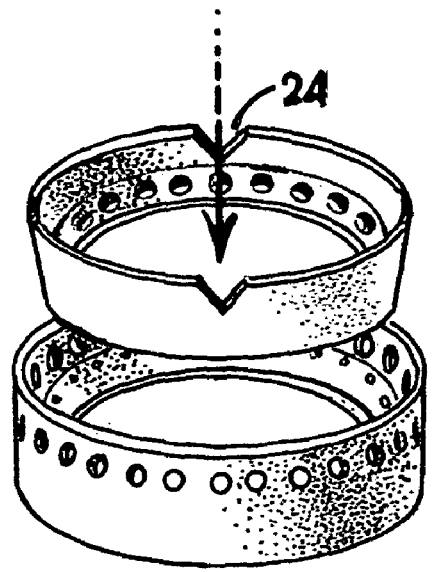

The valve ring is illustrated for example in FIG. 2 as 20 and also has also a generally well-shaped configuration with a vertical shelf 22 and an L shaped cross section. The vale ring is configured and sized to be captively held inside of the anchoring ring in assembly. The valve ring is preferably provided with slits or alternatively "v" shaped formations 24 in the vertical shelf 22 of its L shaped cross section to impart sufficient circumferential resiliency so that upon assembly, the valve ring circumferentially yields and resiliently and sealingly snaps into position within the anchoring ring. Optionally or additionally, the well shaped configuration of the valve ring may be slightly tapered down in the direction of insertion of the valve ring into the anchoring ring to facilitate assembly.

The valve ring (22 in FIG. 2, 44 in FIG. 4,) is provided with circumferential apertures 21 on the bottom flange portion 23 of the L shaped configuration. For the Mitral position, the prosthetic valve 43 is assembled such that its sewing cuff 42 (see FIG. 4) sealingly abuts the underside of the bottom ring portion 23 of the valve ring. For the Aortic position, the prosthetic valve 43 is assembled inside the valve ring. The apertures 21 of the valve ring are used to accommodate a plurality of sutures for permanently fastening the sewing cuff 42 of the Dacron prosthetic replacement valve 43 (see FIG. 4).

After satisfactorily verifying the size of the anchoring ring which the surgeon wants to fasten and implant, an ASD tool comprising a staple holder-dispenser of a suitable and matching size, is taken and passed through the annulus. As the holder is snug in the annulus, it holds the surrounding tissues firmly. The holder may also equipped with the selected anchoring ring, staples and a staple dispensing tool, and with the holder in place, the staples are deployed and fired into the apertures 11 to fasten the anchoring ring in the patient annulus. The surgeon places the anchoring ring in such a manner that the staples engage the maximum thickness of the annulus tissue available.

Figure 3:
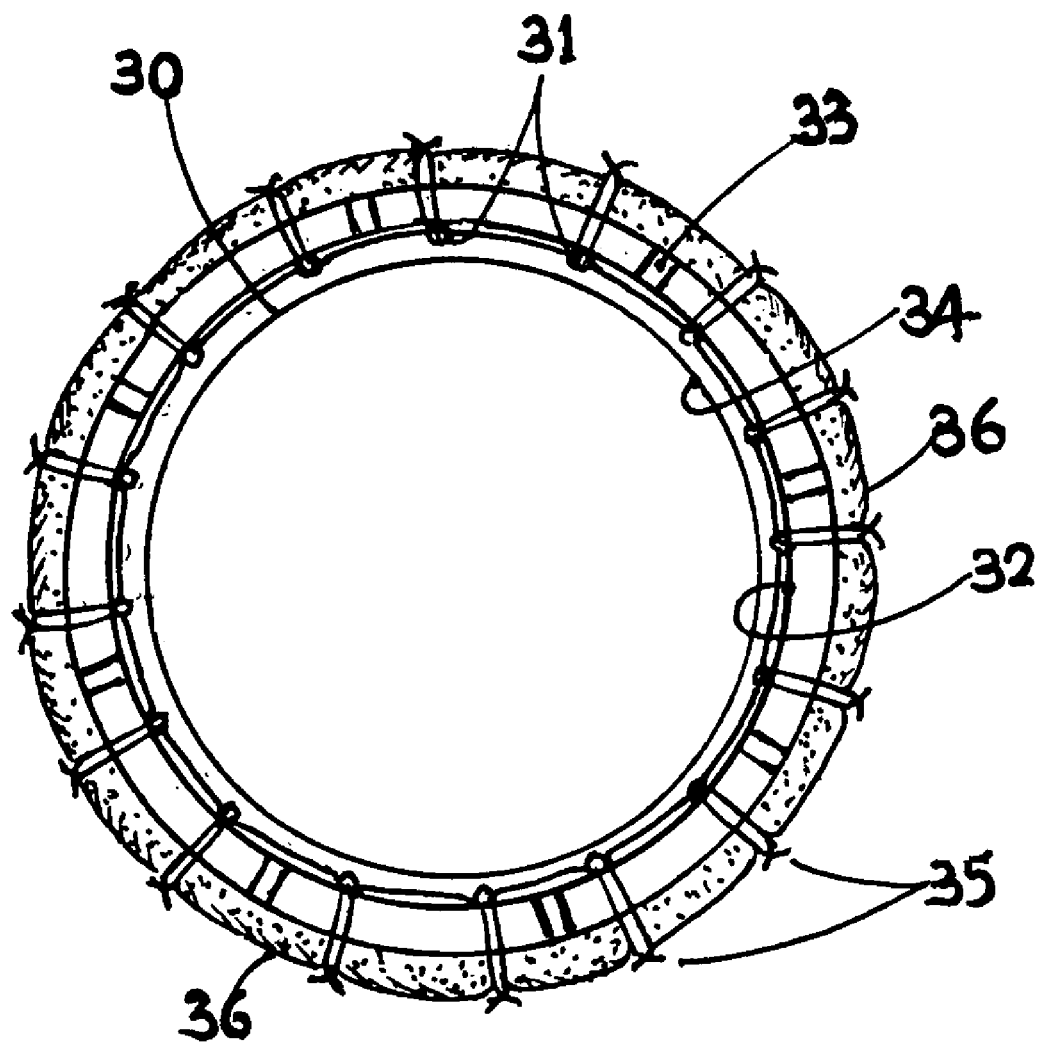
FIG. 3 illustrates dispensing of the staples to fasten the anchoring ring and the patient annulus.
Figure 5:
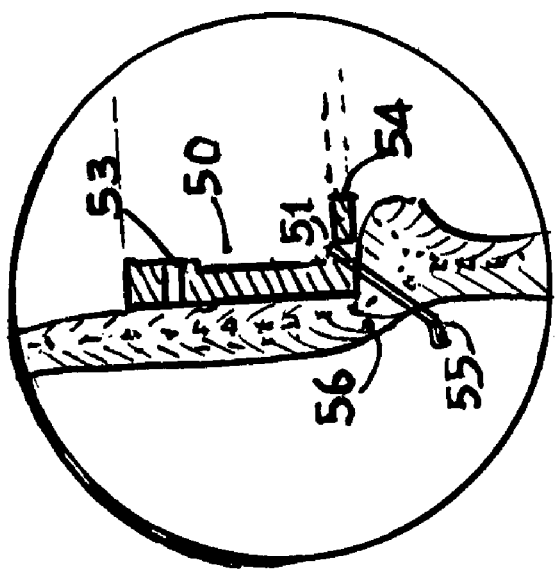
FIG. 5 illustrates a cross section of the patient's annulus along with the Anchoring ring positioned and stapled to the annulus tissue; and, FIG. 6 illustrates an exemplary circular stapling tool which is an Automatic Staple Dispenser (ASD) for stapling and fastening the anchoring ring to the patient's annulus, as used in implementing the present invention.

The staples used are nonmagnetic also, and are preferably made of Nitinol® which has memory features. FIG. 5 shows a cross section of the patient annulus along with a cross section of the anchoring ring which is stapled. FIG. 3 illustrates one implementation showing the manner in which staples are deployed to enter and engage apertures 11 in the anchoring ring 10. The staples are expediently preformed with their free ends bent inwards which can be temporarily straightened to deploy like natural staples. When the staples are fired in assembly by the ASD, the free ends of the staples pass through apertures 11 in the anchoring ring and penetrate the annulus tissue. By virtue of the memory that the staples have, the bent free ends of the staples spring back in the direction of each other to hold and fasten the anchoring ring to the patient's annulus tissue firmly. See FIG. 5 to visualize a cross section of the patient annulus after the anchoring ring is stapled into position.

Parallelly, when the stapling and fastening of the anchoring ring in the patient's annulus is in progress, the selected valve ring 20 (with configuration generally illustrated in FIG. 2) is arranged outside of the patient, positioned (for Mitral installation) as shown at 44 in FIG. 4 over the sewing cuff (Dacron ring) 42 of the prosthetic valve and permanently sutured with several non-absorbable sutures by the surgical group. The suturing is done using the valve ring apertures 21 for passing the sutures through the sewing cuff 42 which is placed under the valve ring 44 as shown in FIG. 4. This process of suturing the valve ring to the sewing cuff poses less limitations since it is done outside of the patient's body, and can be completed to gain surgery-time while the stapling (and fastening) of the anchoring ring 10 to the patient's annulus is in progress. The patient-machine time is considerably reduced. After the permanent suturing of the sewing cuff 42 to the valve ring 44 is done outside of the patient, the valve ring 20 along with the sutured prosthetic valve is pushed into the anchoring ring cavity for assembly.

In assembly, the valve ring 44 (20) along with its sutured prosthetic valve 41 clicks into position within the anchoring ring 10, and is captively held and retained within the installed anchoring ring 10. The surgeon makes sure that the prosthetic valve is positioned in the center of the orifice. After ensuring that the valve ring 44 (20) along with the sutured prosthetic valve 41 (with three leaflets as shown) is firmly attached to the anchoring ring 10, if necessary, three or more commissural sutures may expediently be placed and sutured to the holes 13 on the anchoring ring 10. Thus the surgeon might make sure that the prosthetic valve 41 along with the assembled valve ring 44 (20) stays in place and does not get subjected to any untoward movement. Since the sewing ring of the prosthetic valve does not project radially beyond the inner valve ring, neither the anchoring ring nor the inner valve ring will interfere with the leaflet motion of the prosthetic valve.

An exemplary Mitral valve Replacement Procedure using ASD includes the following: The Mitral valve of the patient is exposed through any standard incision, and part or most of the mitral valve is excised as necessary. The mitral annulus size of the patient is measured with the standard valve sizer, to determine the required size of the anchoring ring/valve ring set for the patient. As stated earlier, the size of the required anchoring ring/valve ring set may be determined otherwise, by known imaging techniques to save time during the surgical procedure. The anchoring ring is stapled to the mitral annulus preferably with the use of powered tool using the apertures 11 provided in the anchoring ring. Alternatively, a non-power tool may be deployed. Such tools are known to those skilled in the art and are not extensively dwelt upon in this text. The prosthetic Mitral valve is sutured to the valve ring outside of the patient (FIG. 4).

As described and illustrated, the valve ring (along with the sutured prosthetic valve) is captively assembled within the already stapled anchoring ring whereby the valve-ring-shelf resiliently goes through the central opening of the anchoring ring into the left ventricular cavity. The valve ring is captively held in the anchoring ring as assisted by the shelf groove 15 of the anchoring ring. Any additional reinforcing sutures if necessary can be placed on the atrial wall and sutured into the holes 13 on the anchoring ring depending on the judgment of the surgeon. Finally, Atriotomy is closed.

Mitral Valve Replacement if the valve is a mechanical type: A similar technique as described above can be used while implanting a mechanical mitral valve. Since the mono or bi-leaflet valve is within the periphery of the inner valve ring and does not project beyond the inner valve ring, neither the anchoring ring nor the valve ring will interfere with the leaflet motion of the prosthetic valve.

FIG. 3 illustrates an example of the staple dispensing arrangement used in the present invention for fastening the anchoring ring to the patient annulus. More particularly, FIG.

3 shows a circular view of the anchoring ring 30, having a vertical surface 32 and a horizontal flange portion 34, the surface 32 and the horizontal flange portion corresponding to flange 14 of the anchoring ring having an L shaped cross section as explained earlier. The anchoring ring includes a plurality of apertures 31 at the meeting portion of the two limbs of the L cross section, the apertures 31 being circumferentially spaced and distributed uniformly around the anchoring ring periphery. Staples 35 are aligned and straightened at their loose ends by the ASD tool (FIG. 6) to pass through the apertures 31 in the anchoring ring and penetrate the tissue of the patient's annulus 36. The surgeon places the anchoring ring in the patient annulus in such a manner that the staples engage the maximum amount of annulus tissue available. Reference may be had to the illustration in FIG. 5 in this context. The staples are preferably made of memory-metal, e.g., Nitinol. The staples are so preformed and configured, that on deployment their bent ends at the ends of their legs spring back because of their memory. Thus the deployed staples hold and fasten the anchoring ring to the patient annulus as shown in FIG. 5. When the staples are pushed through the holes 31 of the anchoring ring as illustrated in FIG. 3 and FIG. 5 to penetrate the patient annulus, expediently, this will give a circumferential purchase of at least 5 mm of annulus tissue all around.

As referenced earlier, the staples are pre-bent at the ends of their legs (FIG. 3), but temporarily, the legs are held straight in the dispenser-holder before they are fired. After the staples are fired, their free ends pass through the holes 31 (of the anchoring ring) and penetrate through the patient annulus and are deployed to resume their preformed shape where the staple free ends face each other to effectively hold the annulus tissue. Because of the memory Nitinol has, the staples effectively hold and fasten the anchoring ring to the annulus tissue of the patient.

The length of the staples, as an example, ranges from 10 to 12 mm, and the numbers of the staples may vary from 20 to 30 distributed all around the anchoring ring. Each hole 31 in the anchoring ring preferably receives two staple-legs from two adjacent staples, i.e., the distal end of a preceding staple and the beginning end of the following staple, as illustrated in FIG. 3. The foregoing staple layout is found to be effective in fastening the anchoring ring to the patient annulus to minimize blood leakage after the valve installation . . . . Additionally as aforesaid, the surgeon has the option of providing a few quick reinforcing sutures between the anchoring ring and the patient annulus, if desired. For this purpose, a set of additional apertures shown at 33 in FIG. 3 (13 in FIG. 1) may be used.

FIG. 4 is an illustration of how the valve ring is placed in preparation for being sutured outside the patient's body to the sewing cuff of the prosthetic valve. Illustrated in FIG. 4 is the valve ring 44, and placed underneath is the prosthetic valve 41 which includes a sewing cuff 42 and the three leaflets 43 (the valve being a tri-cusped valve). The sutured sewing ring (of the Dacron prosthetic valve) does not radially extend beyond the valve ring. As described earlier, the fastening of the prosthetic valve to the valve ring 44 (also see FIG. 2) outside of the patient's body provides a distinct time advantage and reduces the patient-machine time. This approach also obviates the surgeon having to work with the sewing ring of the prosthetic valve in a limited space, unlike if the prosthetic valve installation is been done in a traditional manner.

FIG. 5 shows an exploded view of a portion of the patient's annulus 56 and the assembled anchoring ring 50 with the staples 55 deployed. Also shown in FIG. 5 are the apertures 51 (apertures 11 in FIG. 1) through which the staples pass, and also the additional apertures 53, corresponding to the apertures 13 in FIG. 1.

Figure 6:
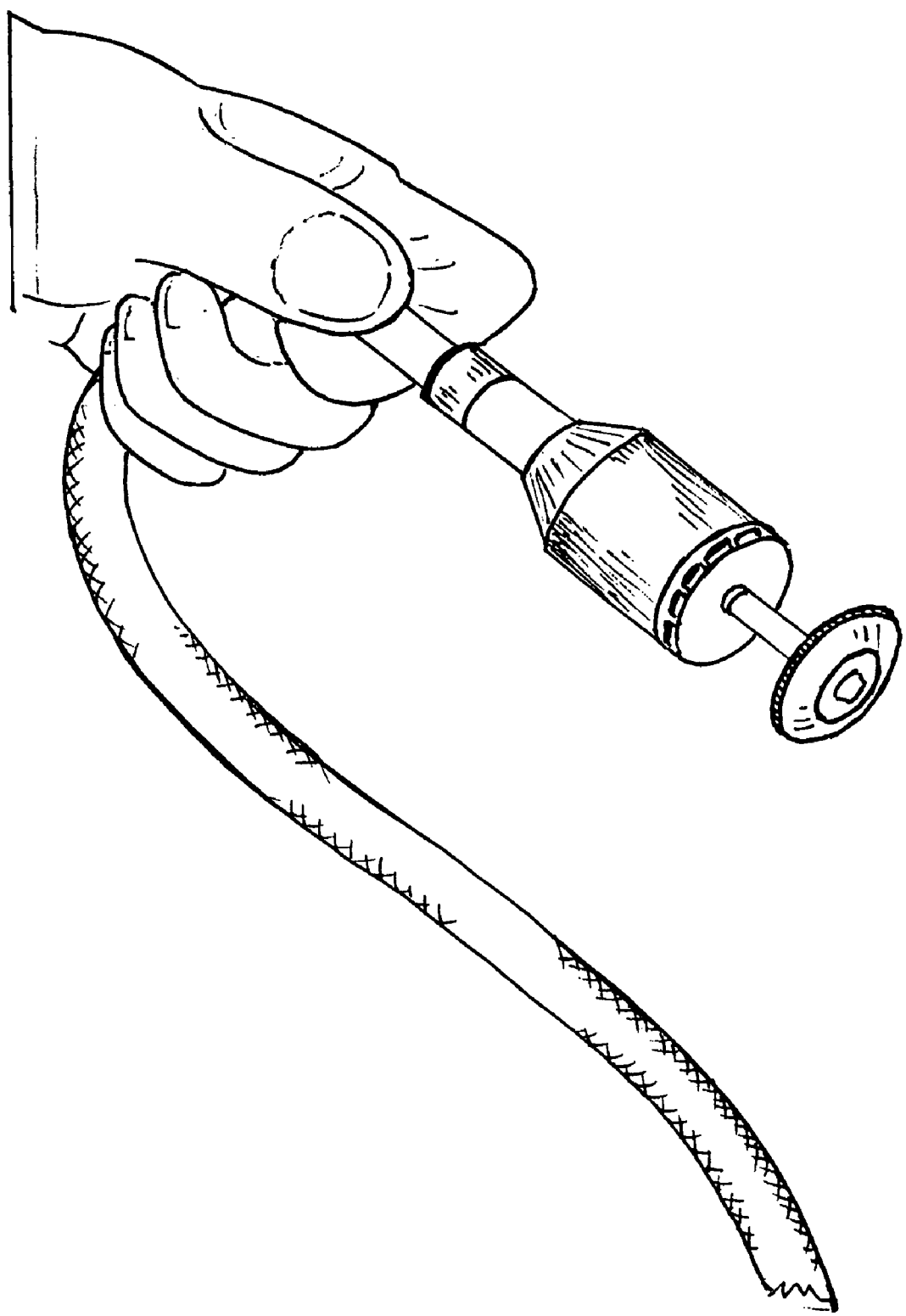

FIG. 6 shows an example of a staple dispensing and installing tool. The tools include a flexible shaft to negotiate the anchoring ring towards the valve annulus. The flexible shaft includes a tip having a center cylinder which is chosen to have a suitable size. The appropriate sized cylinder for the size of the annulus is selected and the anchoring ring along with the stapling device is passed over it. The annulus size generally can be from 19 mm-29 mm, depending on the patient. The appropriate sized cylinder is passed through the annulus and into the ventricular cavity until the anchoring ring touches the annulus. Keeping it snug to the annulus, the stapling device is fired to fasten the properly located anchoring ring to the patient's valve annulus. The description does not dwell on further details of the tool in FIG. 6, since those who are skilled in the art are familiar with tools of this type.

The following narrates at least some of the desirable features of the method, system and design as described herein: easily implantable; ensure a high level of reliability; no narrowing of the natural valve orifice; no interference with prosthetic valve leaflet motion; not produce a new source of systemic emboli; offer ability to incorporate into body tissues; obviate use of undue amounts of anticoagulation; no creation of perivalvular leaks; Hemolysis not caused; enable reinforcement with additional sutures easily if necessary; and, removal possible if necessary.

Other desirable requirements and features of the prosthetic replacement valve of the present design include the following: In the aortic position, the valve does not injure or obstruct coronary ostia; does not injure the conduction system; does not interfere with the mitral leaflet motion; does not interfere with aortic closure; and is able to be inserted through a mini surgical incision. In the mitral position, the valve of the present design does not injure the circumflex coronary artery; does not occlude coronary sinus; is able to work even if part or whole of native mitral valve is left in place; will not distort or pull on aortic valve leaflets; and is able to be inserted through a mini surgical incision.

The following desirable requirements in prosthetic valves design were met by the present two ring design and the present installation method: the material may be metal and: should have sufficient strength;
should not easily break;
should have history of proven human implantability;
should be non allergic;
should be able to combine with other metals; and
should be non magnetic.

It is to be understood that the stapling of the anchoring ring to the patient annulus in the present valve design may be done using a manually operated tool or a power tool. If a power tool, it could be battery powered or electrically powered. If the stapling tool has powered components, the advantages of having powered components render the sapling tool quick to staple, and ensure precision and consistency in delivery. With powered components, the staples can desirably penetrate through some calcified areas of the patient annulus.

If the stapling device has non-powered components, the features to note are that it is simple to use, and despite relatively less precision and can be used by surgeons as well as less experienced personnel such as trainees.

Materials chosen for the anchoring ring and the valve ring in the present design: The materials chosen for the anchoring ring should generally be nonmagnetic and should be capable of incorporation into the human body, so that no rejection problems are encountered. The material used for the anchoring ring and the valve ring in the present design is preferably Titanium coated with Tantalum-porous-metal which combination would offer the advantages of making the rings non corrosive and strong, and provide a proven acceptance in tissue in growth. Other alternative materials and metals or alloys are acceptable for use for the ring-material, and are within the ambit of the present invention.

Materials for the staples in the present design: The preferred material chosen for the staples as aforesaid is preferably Nitinol®, and the staples are used to fasten and hold the Anchoring ring into the tissues in the region of the patient annulus. It is noted that Nitinol has specific memory characteristics, and has already been used and accepted in the arterial system.

The following exemplary features in the design concept of the present invention are noted: The design uses two ring components to hold the prosthetic valve to the Aortic or Mitral (Tricuspid) annulus. The first ring (anchoring ring) is stapled to the native valve annulus with an optional powered tool. The second ring (valve ring) is sewn to the Dacron fabric (sewing cuff) of the prosthetic valve and is captively assembled into the first ring like a template. Once assembled, the valve ring will not easily dislodge from within the anchoring ring.

The two ring concept with the prosthetic valve sutured to the inner valve ring, and the metals chosen in this implementation as described above will facilitate easy implantation of prosthetic valves in the heart and should significantly decrease the cardiopulmonary bypass time.

In the foregoing detailed description of embodiments of the invention, various features are grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the detailed description of embodiments of the invention, with each claim standing on its own as a separate embodiment. It is understood that the above description is intended to be illustrative, and not restrictive. It is intended to cover all alternatives, modifications and equivalents as may be included within the spirit and scope of the invention as defined in the appended claims. Many other embodiments will be apparent to those of skill in the art upon reviewing the above description. The scope of the invention should therefore be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "horizontal," "vertical", etc., are used merely as labels, and are not intended to impose limitations or specific requirements on their objects.

The invention claimed is:

1. A prosthetic heart valve replacement system for valve replacement in a patient's valve annulus during surgery, enabling a reduction of time duration that the patient is subjected to a heart-lung machine during prosthetic heart valve replacement, comprising:
a first outer anchoring ring which is flanged and fastened to the patient's heart valve annulus during surgery, and a second inner valve ring which is flanged and to which a prosthetic heart valve is attached outside of the patient, such as by suturing; the second inner valve ring being configured to be assembled to be captively and snugly held concentrically inside of said first outer anchoring ring,
wherein said first outer anchoring ring and said second inner valve ring are made of material which remains noncorrosive even when subjected to prolonged use inside of the patient's heart, and wherein the first outer anchoring ring and the second inner valve ring each have a generally tubular configuration with a horizontal inwardly projecting flange at one end, the second inner valve ring being configured to be circumferentially resilient when compressed radially inwards, so as to be captively held within the first outer anchoring ring upon assembly.

2. The prosthetic heart valve replacement system as in claim 1, wherein the material of the first outer anchoring ring and the second inner valve ring comprises Titanium.

3. The prosthetic heart valve replacement system as in claim 2, wherein the material of the first outer anchoring ring and the second inner valve ring comprises Titanium with a coating of Tantulum porous metal.

4. The prosthetic heart valve replacement system as in claim 1, wherein the first outer anchoring ring has an L shaped cross section with a vertical shelf, the vertical shelf being provided at the L shaped cross-section-bottom with a plurality of apertures circumferentially disposed along a lower end of the shelf, said outer anchoring ring being stapled to the patient's annulus using staples which pass through said apertures, said staples having a memory characteristic and being preformed for being dispensed by a mechanical stapling device.

5. The prosthetic heart valve replacement system as in claim 1, wherein the first anchoring ring, the second inner valve ring and staples comprise nonmagnetic material, and wherein said second inner valve ring is provided with notches in its configuration to provide radially inward resiliency.

6. The prosthetic heart valve replacement system as in claim 3, wherein said horizontal inwardly projecting flange of the first outer anchoring ring has an undersurface which is uneven to be conducive in use to hug the patient's valve annulus tissue tightly.

7. The prosthetic heart valve replacement system as in claim 4, wherein the first outer anchoring ring is provided with a second set of apertures which may be used for sutures for providing added fastening of the first anchoring ring to the patient's annulus in addition to the fastening provided by the staples.

8. A two-ring prosthetic heart valve replacement system for valve replacement in a patient's heart valve annulus during surgery, enabling a reduction of time duration that the patient is subjected to a heart-lung machine during the prosthetic heart valve replacement, comprising:
a first outer anchoring ring with a tubular configuration with a shelf at one end and a radially inwardly projecting flange integrally formed at the other end of the tubular configuration, said first outer ring being separately stapled, fastened and installed in the patient's heart valve annulus during surgery; and,
a second inner valve ring which is also provided with an open tubular configuration and an integrally formed radially inwardly extending apertured flange configured for attachment to the prosthetic heart valve such as by suturing which is done outside of the patient;
said second inner valve ring being permanently sutured to the prosthetic heart valve and being configured to be resilient radially inwards to facilitate assembly thereof concentrically inside of the first outer anchoring ring for being captively and snugly held therein.

9. The prosthetic heart valve replacement system as in claim 8, wherein the outer anchoring ring and the valve ring are made of material which remains noncorrosive even when subjected to prolonged use inside of the patient's heart, said second inner valve ring being provided with "v" shaped grooves at its open end, said tubular configuration of the second inner valve ring being shaped to taper down towards its said radially inwardly projecting flange.

10. The prosthetic heart valve replacement system as in claim 9, wherein the material of the first outer anchoring ring and the second inner valve ring comprises Titanium.

11. The prosthetic heart valve replacement system as in claim 10, wherein the material of the first outer anchoring ring and the second inner valve ring comprises Titanium with a coating of Tantulum porous metal.

12. The prosthetic heart valve replacement system as in claim 9, wherein the outer anchoring ring is provided with apertures for being stapled to the patient's annulus using staples which have a memory characteristic and are preformed for being dispensed by a mechanical stapling device.

13. The prosthetic heart valve replacement system as in claim 12, wherein the first outer anchoring ring, the second inner valve ring and the staples comprise nonmagnetic material.

14. The prosthetic heart valve replacement system as in claim 12, wherein the staples have memory and are each provided with two legs having bent tips which face each other, the staples being configured for being dispensed using a powered stapling device.

15. The prosthetic heart valve replacement system as in claim 8, wherein the inwardly extending flange of the first anchoring ring has an undersurface which is uneven to be conducive to hug the patient's valve annulus tissue tightly in assembly.

16. The prosthetic heart valve replacement system as in claim 12, wherein the tubular configuration of the first outer anchoring ring is provided with a radially inward step to captively accommodate in assembly, the end the inner valve ring which is provided with said "v" grooves, the first outer anchoring ring being also provided with a second set of apertures which may be used for sutures for providing added fastening of the first anchoring ring to the patient's annulus in addition to the fastening provided by the staples.

* * * * *